United States Patent [19]
Potter

[11] 4,158,675
[45] Jun. 19, 1979

[54] MANUFACTURE OF HALOGENATED COMPOUNDS

[75] Inventor: Stephen E. Potter, Runcorn, England

[73] Assignee: Imperial Chemical Industries Limited, London, England

[21] Appl. No.: 875,933

[22] Filed: Feb. 7, 1978

[30] Foreign Application Priority Data

Sep. 23, 1977 [GB] United Kingdom ............... 39721/77

[51] Int. Cl.² .............................................. C07C 17/08
[52] U.S. Cl. ................................ 260/653.7; 260/653.8
[58] Field of Search ...................................... 260/653.7

[56] References Cited

U.S. PATENT DOCUMENTS

| | | | |
|---|---|---|---|
| 2,885,427 | 5/1959 | Ruh et al. | 260/653.7 |
| 3,755,477 | 8/1973 | Firth et al. | 260/653.7 |

Primary Examiner—C. Davis
Attorney, Agent, or Firm—Cushman, Darby & Cushman

[57] ABSTRACT

Manufacture of 1,1,1,2-tetrafluoroethane by reacting 1,1,1-trifluoro-2-chloroethane with hydrogen fluoride in the presence of a chromium oxide catalyst and removing 1,1-difluoro-2-chloroethylene contaminant from the resulting impure asym tetrafluoroethane product by passing the impure product with hydrogen fluoride over a chromium oxide catalyst at much lower temperatures than are used in the manufacturing process.

10 Claims, No Drawings

MANUFACTURE OF HALOGENATED COMPOUNDS

This invention relates to a process for the manufacture of 1,1,1,2-tetrafluoroethane and in particular to such a process wherein said tetrafluoroethane of a high degree of purity is obtained.

A process is disclosed in copending application Ser. No. 875,932 filed on even date herewith for the manufacture of 1,1,1,2-tetrafluoroethane which comprises reacting in the vapour phase at elevated temperature, suitably in the range 300° C. to 400° C., a haloethane of formula $CX_3CH_2Y$ wherein X is bromine, chlorine or fluorine and Y is either bromine or chlorine with hydrogen fluoride in the presence of a catalyst which is chromium oxide or which is at least in part basic chromium fluoride.

In said process the chromium oxide catalyst may consist of chromium oxide alone. The chromium oxide may be activated by heating in an inert atmosphere. Again the catalyst may comprise a basic chromium fluoride in which chromium is associated with oxygen and fluorine atoms. When employing a chromium oxide catalyst prepared by heating a readily-decomposable salt of chromium e.g. chromic hydroxide in air or oxygen as described in our U.S. Pat. No. 3,426,009 useful yields of the desired 1,1,1,2-tetrafluoroethane may be obtained.

It is particularly preferred in said process to employ a chromium oxide catalyst which is obtained by treating a chromium hydroxide paste in an atmosphere comprising 10 to 100 percent by weight of steam at temperatures of 50° C. to 180° C. for at least one hour and subsequently drying and calcining the product as is more fully described and claimed in our U.S. Pat. No. 3,755,477. The catalyst may be compressed into pellets and used in a fixed bed. Alternatively the catalyst of appropriate particle size may be used in a fluidised bed. The pelleted or non pelleted catalyst may be given a prefluorination treatment by passing hydrogen fluoride over the catalyst at 250° C. to 450° C. for at least 30 minutes. In any event the catalyst may take up variable amounts of fluorine in use.

The amount of hydrogen fluoride employed in said process depends to a great extent on the haloethane starting material. At least the stoichiometric amount of hydrogen fluoride is usually employed per mole of haloethane starting material. It is preferred to employ an excess of the stoichiometric amount but not greater than six times the stoichiometric amount of hydrogen fluoride in the present process. It is particularly preferred to employ at least two moles but not greater than six moles of hydrogen fluoride per mole of said organic starting material, e.g. 1,1,1-trifluoro-2-chloroethane.

Suitable temperatures in said process are in the range 300° C. to 400° C. for example 325° C. to 375° C. Preferred contact times are in the range 2 to 60 seconds. Atmospheric or superatmospheric pressures may be employed.

Unreacted organic starting material, hydrogen fluoride and by-products e.g. haloethanes containing chlorine atoms in the $CX_3$ group may be recycled to the process for further reaction to give the desired compound.

However when the Y substituent in the haloethane starting material is chlorine there may be formed in addition to the desired product asym tetrafluoroethane ($CF_3 CH_2F$) a small amount of 1,1-difluoro-2-chloroethylene ($CF_2=CHCl$) as by-product. This occurs for instance when the organic starting material in the hydrofluorination reaction is 1,1,1-trifluoro-2-chloroethane.

It is desirable to reduce further even small amounts of said difluorochloroethylene but this is extremely difficult to achieve by conventional methods, for example by fractional distillation.

We have now found that said difluoroethylene impurity contained in asym tetrafluoroethane may be reduced in content by treating the impure asym tetrafluoroethane with hydrogen fluoride in the presence of catalysts used in said process for manufacture of asym tetrafluoroethane at temperatures in the range 100° C. to 275° C. which are much lower than those used in said manufacture of 1,1,1,2-tetrafluoroethane.

The purification process of the present invention is broadly applicable to the purification of asym tetrafluoroethane containing difluorochloroethylene as impurity, whatever the source of the impure asym tetrafluoroethane. The purification process is, however, especially applicable to the asym tetrafluoroethane product obtained by the process described in our said copending Application.

According to a feature of the present invention we provide a process for the manufacture of 1,1,1,2-tetrafluoroethane which comprises reacting in the vapour phase at elevated temperatures a haloethane of formula $CX_3CH_2Y$ wherein X is bromine, chlorine or fluorine and Y is chlorine with hydrogen fluorine in the presence of a catalyst which is chromium oxide or which is at least in part basic chromium fluoride and wherein the 1,1,1,2-tetrafluoroethane product containing 1,1-difluoro-2-chloroethylene as impurity is brought together with hydrogen fluoride into contact with said catalyst which is chromium oxide or which is at least in part basic chromium fluoride at a temperature in the range 100° C. to 275° C. whereby said haloethylene content is reduced.

The impure asym tetrafluoroethane to be treated to remove the haloethylene impurity may be the crude product which is associated with other haloethanes containing fluorine including one or more of 1,1,1,2,2-pentafluoroethane ($CF_3 CHF_2$), 1,1,1,2-tetrafluoro-2-chloroethane ($CF_3 CHClF$), 1,1,1-trifluoroethane ($CF_3 CH_3$) and 1,1,1-trifluoro-2-chloroethane ($CF_3 CH_2Cl$).

Such a crude reaction product may be obtained by bringing 1,1,1-trifluoro-2-chloroethane into reaction with hydrogen fluoride at temperatures in the range 300° C. to 400° C. in the presence of a catalyst which is chromium oxide or which is at least in part basic chromium fluoride as is previously described.

The manner of carrying out the process of this feature of the invention is capable of considerable variation. In one method the crude impure reaction product obtained by the hydrofluorination of 1,1,1-trifluoro-2-chloroethane comprising asym tetrafluoroethane, said other haloethanes containing fluorine and unreacted hydrogen fluoride leaving a reactor are passed into a second reactor containing a catalyst which is chromium oxide or which is at in least a part basic chromium fluoride and maintained at 100° C. to 275° C. whereby said impurity is almost completely removed. Such a crude reaction product will also be associated with hydrogen chloride derived by reaction of hydrogen fluoride with organic starting material, but such hydrogen chloride need not be removed before passing to the second reactor. In another variant the process is carried out in a single reactor having a first reaction zone containing a catalyst which is a chromium oxide or which is at least in part basic chromium fluoride maintained at a temperature (higher than that of the second zone) of 300° C. to 400° C. wherein the hydrofluorination of 1,1,1-trifluoro-2-chloroethane is effected. The crude impure organic product together with unreacted hydrogen fluoride (and hydrogen chloride) from the first reaction zone is fed to the second part of the reaction zone containing said chromium oxide or basic chromium fluoride catalyst maintained at a temperature of 100° C. to 275° C. whereby the amount of 1,1-difluoro-2-chloroethylene contaminant in the crude product is considerably reduced. Asym-tetrachloroethane may be recovered from the reaction mixture leaving the reactor by conventional means, for example, by fractional distillation.

Preferred temperatures in the purification process are in the range 125° C. to 250° C. Contact times are usually in the range 2 to 20 seconds and preferably in the range 3 to 15 seconds. Atmospheric or superatmospheric pressures may be employed.

1,1,1,2-tetrafluoroethane which has a low boiling point ($-26.5°$ C.) is useful as a refrigerant, for example, in food-freezing techniques. It is useful as an aerosol propellant and as a foam blowing agent.

The following Examples illustrate the invention. All percentages are v/v unless otherwise stated.

EXAMPLE 1

Into a tubular nickel reactor 90 cms long and 2.5 cms internal diameter were placed 130 grams of a chromium oxide catalyst. The latter had been prepared by steam treatment of a chromium hydroxide paste at 95° C. for 18 hours, and subsequently calcined at 340° C. as described in our U.S. Pat. No. 3,755,477. The catalyst was then pretreated with hydrogen fluoride at 350° C. for 4 hours. The tubular reactor was heated by an electric furnace and the temperature inside the reactor was maintained in the range 335° C. to 355° C.

This reactor was connected to a second similar reactor containing the same amount of said catalyst but held at 160° C.

89 grams of 1,1,1-trifluoro-2-chloroethane were passed together with an amount of hydrogen fluoride over the fixed catalyst bed over a total period of 3 hours. The molar ratio of $HF:CF_3CH_2Cl$ was 3:1. The contact time was 7 seconds. The exit gas leaving the reactor was analysed by gas/liquid chromatography and was found to contain (%).

| | |
|---|---|
| $CF_3CH_2F$ | 12.63 |
| $CF_2 = CHCl$ | 0.53 |
| $CF_3CHClF$ | 0.04 |
| OTHERS | 0.375 |
| $CF_3CH_3$ | 0.17 |
| $CF_3CHF_2$ | 0.02 |
| $CF_3CH_2Cl$ | 86.23 |

Said exit gas containing hydrogen fluoride was passed to said second similar reactor the contact time being again 7 seconds. The exit gas leaving the second reactor was analysed by gas/liquid chromatography and was found to contain (%)

| | |
|---|---|
| $CF_3CH_2F$ | 12.63 |
| $CF_2 = CHCl$ | 0.0007 |
| $CF_3CHClF$ | 0.06 |
| OTHERS | 0.1 |
| $CF_3CH_3$ | 0.18 |
| $CF_3CHF_2$ | 0.0005 |

-continued

| | |
|---|---|
| $CF_3CH_2Cl$ | 87.0 |

What is claimed is:

1. A process for the manufacture of 1,1,1,2-tetrafluoroethane which comprises reacting in the vapour phase at elevated temperature a haloethane of formula $CX_3CH_2Y$ wherein X is bromine, chlorine or fluorine and Y is chlorine with hydrogen fluoride in the presence of a catalyst which is chromium oxide or which is at least in part basic chromium fluoride and wherein the 1,1,1,2-tetrafluoroethane product containing 1,1-difluoro-2-chloroethylene as impurity is brought together with hydrogen fluoride into contact with said catalyst which is chromium oxide or which is at least in part basic chromium fluoride at a temperature in the range 100° C. to 275° C. whereby said haloethylene content is reduced.

2. A process as claimed in claim 1 in which in the haloethane starting material X is chlorine and/or fluorine.

3. A process as claimed in claim 2 in which at least one of the X substituents is fluorine.

4. A process as claimed in claim 3 in which the haloethane is 1,1,1-trifluoro-2-chloroethane.

5. A process as claimed in any of the preceding claims wherein a chromium oxide catalyst is employed in the manufacture and purification process which is obtained by treating a chromium hydroxide paste in an atmosphere comprising 10 to 100 molar percent by weight of steam at a temperature of 50° C. to 180° C. for at least one hour and subsequently drying and calcining the product.

6. A process as claimed in claim 1 wherein the organic starting material is 1,1,1-trifluoro-2-chloroethane and in which the resulting crude impure 1,1,1,2-tetrafluoroethane is associated with other haloethanes containing fluorine including one or more of pentafluoroethane, 1,1,1,2-tetrafluoro-2-chloroethane, 1,1,1-tetrafluoroethane and 1,1,1-trifluoro-2-chloroethane.

7. A process as claimed in claim 4 which the crude impure product comprising 1,1,1,2-tetrafluoroethane, said other haloethanes containing fluorine and unreacted hydrogen fluoride leaving the reactor are passed into a second reactor containing a catalyst which is chromium oxide or which is at least in part basic chromium fluoride and maintained at a temperature in the range 100° C. to 275° C.

8. A process as claimed in claim 4 carried out in a single reactor having a first reaction zone containing a catalyst which chromium oxide or at least in part basic chromium fluoride maintained at a temperature of 300° C. to 400° C. to produce said crude impure organic product comprising 1,1,1,2-tetrafluoroethane, other haloethanes and unreacted hydrogen fluoride which is fed to a second part of the reaction zone containing said chromium oxide or basic chromium fluoride catalyst maintained at a temperature in the range 100° C. to 275° C. whereby the amount of 1,1-difluoro-2-chloroethylene contaminant is reduced.

9. A process as claimed in claim 1 in which the purification of the asym-tetrafluoroethane is carried out at a temperature in the range 125° C. to 250° C.

10. A process for the reduction of 1,1-difluoro-2-chloroethylene impurity contained in 1,1,1,2-tetrafluoroethane which comprises treating the impure 1,1,1,2-tetrafluoroethane with hydrogen fluoride in the presence of a catalyst which is chromium oxide or which is at least in part basic chromium fluoride at temperatures in the range of 100° C. to 275° C. whereby said haloethylene content is reduced.

* * * * *